(12) United States Patent
Myers et al.

(10) Patent No.: US 10,329,226 B2
(45) Date of Patent: Jun. 25, 2019

(54) PROCESS FOR THE PRODUCTION OF CHLORINATED METHANES

(71) Applicant: BLUE CUBE IP LLC, Clayton, MO (US)

(72) Inventors: John D. Myers, Clayton, MO (US); Matthew L. Grandbois, Clayton, MO (US)

(73) Assignee: Blue Cube IP LLC, Clayton, MO (US)

( * ) Notice: Subject to any disclaimer, the term of this patent is extended or adjusted under 35 U.S.C. 154(b) by 0 days.

(21) Appl. No.: 15/759,728

(22) PCT Filed: Sep. 22, 2016

(86) PCT No.: PCT/US2016/053042
§ 371 (c)(1),
(2) Date: Mar. 13, 2018

(87) PCT Pub. No.: WO2017/053528
PCT Pub. Date: Mar. 30, 2017

(65) Prior Publication Data
US 2018/0258016 A1    Sep. 13, 2018

Related U.S. Application Data

(60) Provisional application No. 62/221,856, filed on Sep. 22, 2015.

(51) Int. Cl.
| | | |
|---|---|---|
| *C07C 17/04* | (2006.01) |
| *C07C 17/10* | (2006.01) |
| *C07C 17/25* | (2006.01) |
| *C07C 19/03* | (2006.01) |
| *C07C 19/04* | (2006.01) |
| *C07C 19/05* | (2006.01) |
| *C07C 21/10* | (2006.01) |
| *C07C 17/013* | (2006.01) |
| *C07C 17/383* | (2006.01) |
| *C07C 17/395* | (2006.01) |
| *C07C 19/041* | (2006.01) |
| *C07C 19/043* | (2006.01) |
| *C07C 19/045* | (2006.01) |
| *C07C 19/055* | (2006.01) |

(52) U.S. Cl.
CPC ............ *C07C 17/013* (2013.01); *C07C 17/04* (2013.01); *C07C 17/10* (2013.01); *C07C 17/25* (2013.01); *C07C 17/383* (2013.01); *C07C 17/395* (2013.01)

(58) Field of Classification Search
CPC ....... C07C 17/395; C07C 19/03; C07C 19/04; C07C 19/041; C07C 17/10; C07C 19/043; C07C 19/045; C07C 17/25; C07C 17/04; C07C 19/05; C07C 19/055; C07C 17/383
See application file for complete search history.

(56) References Cited

U.S. PATENT DOCUMENTS 3,848,007 A * 11/1974 Forlano .................. C07C 19/01
570/241

* cited by examiner

*Primary Examiner* — Jafar F Parsa
(74) *Attorney, Agent, or Firm* — Polsinelli PC (57) ABSTRACT

The present invention provides processes for the production of chlorinated methanes via the direct chlorination of methane. The processes include a dehydrochlorination and/or chlorination step that converts up to 100% of the higher chlorinated alkanes in a process stream from the methane chlorination reaction into more highly chlorinated alkanes. These more highly chlorinated alkanes can be easily removed from the process stream. The use of a cost effective feedstream of crude methane is thus rendered possible, without additional capital expenditure for the sophisticated separation equipment required to separate ethane and other hydrocarbon components from the methane feed.

19 Claims, 6 Drawing Sheets

PROCESS FOR THE PRODUCTION OF CHLORINATED METHANES

FIELD OF THE INVENTION

The present disclosure generally relates to processes for the production of chlorinated methanes.

BACKGROUND OF THE INVENTION

Chlorinated methanes such as methyl chloride, methylene chloride, chloroform, and carbon tetrachloride are commonly used as chemical reactants, solvents, propellants, and herbicides. One common method of preparing chlorinated methanes is to directly chlorinate methane, while another common method involves the hydrochlorination of methanol to produce methyl chloride, which is further chlorinated to provide the desired end product(s). Though the direct chlorination of methane is economically advantageous, the hydrochlorination of methanol is more common.

The primary reason direct chlorination is not more widely used can be attributed to the fact that methane (i.e., natural gas) is typically not pure. Natural gas normally contains other components, such as ethane and higher alkanes. Once chlorinated, such components can be difficult to remove from a process stream comprising chlorinated methanes. As an illustrative example, 1,1,-dichloroethane, produced via the chlorination of ethane, is difficult to separate from chloroform on an industrial process scale, because their boiling points are similar: 1,1-dichloroethane's boiling point is 135° F. (or 57.2° C.), while chloroform's boiling point is 142.2° F. (or 61.2° C.).

Purifying natural gas by removing components such as ethane from the methane feed stream is expensive and requires energy-intensive cold box or other purification technologies. In order to use methane in the production of high-quality chlorinated methanes, low levels of these impurities are needed. Using high purity methane in a direct chlorination reaction will produce high purity chlorinated methanes, but again, obtaining the high purity methane is expensive.

A process for the production of chlorinated methanes via the direct chlorination of an inexpensive methane gas feed stock, such as natural gas, is needed. Such a process would avoid expensive methane purification techniques, and would lower the production costs associated with the formation of chlorinated methanes.

SUMMARY OF THE INVENTION

In one aspect, disclosed herein are efficient processes for the production of chlorinated methanes via the direct chlorination of a crude methane feedstock (natural gas). The process further includes one or more dehydrochlorination and/or chlorination reactions, which convert the non-methane based alkanes into higher chlorinated alkanes and alkenes, while not affecting the chlorinated methanes. In one embodiment, the dehydrochlorination and/or the chlorination reactions are thermal reactions. In another embodiment, the dehydrochlorination and/or the chlorination reactions occur in the presence of at least one catalyst. The use of at least one catalyst is preferred. When conducted on a feedstream comprising chlorinated alkanes and chlorinated methanes, the process converts almost all of the chlorinated alkanes into higher chlorinated alkanes, i.e., chlorines are added to the alkane, which are more easily separated from the desired, chlorinated methanes. The chlorinated alkanes may be dehydrochlorinated and/or chlorinated in the same reactor or in a reactive distillation column for additional processing efficiencies.

In another aspect, a process for the production of chlorinated methanes is disclosed. The process comprises chlorinating a feedstream comprising methane and ethane in a methane chlorination reactor to produce a process stream comprising chlorinated methanes, mono- and dichlorinated ethanes, chlorinated ethylenes, and higher chlorinated alkanes. At least a portion of the process stream comprising chlorinated methanes, mono- and dichlorinated ethanes, chlorinated ethylenes, and higher chlorinated alkanes is subjected to conditions effective to dehydrochlorinate and/or chlorinate the non-methane based alkanes. The process stream after the dehydrochlorination and/or chlorination provides higher chlorinated ethanes, i.e., ethanes having more than two chlorine atoms such as tri-, tetra-, penta- or hexachlorinated ethanes. The mono- and dichlorinated ethanes, chlorinated ethylenes, and higher chlorinated alkanes may be dehydrochlorinated and/or chlorinated in the same reactor for additional processing efficiencies. Once the process stream comprising the mono- and dichlorinated ethanes, chlorinated ethylenes, and higher chlorinated alkanes has been dehydrochlorinated and/or chlorinated, one or more of the resulting higher chlorinated ethanes are readily separated to provide a product stream comprising chlorinated methanes substantially free of ethanes, chlorinated ethanes, or chlorinated ethylenes. In some embodiments, the product stream may consist essentially of methyl chloride, dichloromethane, trichloromethane and/or tetrachloromethane. In other embodiments, the product stream may consist of methyl chloride, dichloromethane, trichloromethane and/or tetrachloromethane. In many, if not all embodiments, the product stream will comprise a lesser amount of ethane and/or chlorinated ethanes and/or chlorinated ethylenes than the process stream from the methane chlorination reactor.

Other features and iterations of the invention are described in more detail below.

DETAILED DESCRIPTION OF THE INVENTION

In one aspect, the processes for preparing highly purified chlorinated methanes comprise contacting a feed stock of natural gas and a chlorinating agent in vapor or gas phase. The chlorinated methane process stream comprising chlorinated methanes, mono- and dichlorinated ethanes, chlorinated ethylene, and higher chlorinated alkanes are fed into a dehydrochlorination/chlorination process. The chlorinated methanes are essentially unaffected while the non-methane based materials, e.g., mono- and dichlorinated ethanes, chlorinated ethylenes, and higher chlorinated alkanes undergo dehydrochlorination/chlorination to provide higher chlorinated alkanes, such as tetra-, penta-, and hexachlorinated ethanes. The contents from the process may be readily purified yielding high purity chlorinated methanes.

(I) Chlorination of Natural Gas

The process for preparing highly purified chlorinated methane commences by contacting a feed stream comprising natural gas and a chlorinating agent.

(a) Natural Gas Feed Stream

The process makes use of crude methane. Crude methane, also commonly known as natural gas may be produced by any natural gas production process. Generally, natural gas may typically include up to 20 weight % of impurities. These impurities comprise higher alkanes such as ethane, propane, butane, pentanes, and higher molecular weight hydrocarbons. Other impurities present in the natural gas feed stream comprise nitrogen, carbon dioxide and even small amounts of sulfur compounds.

In various embodiments, the impurities in the natural gas feed stream may be less than 25 weight %, less than 20 weight %, less than 15 weight %, less than 10 weight %, less than 5 weight %, less than 1 weight %, or less than 0.1 weight %. Stated another way, the methane used as a feedstock may comprise from 0.1 wt % to 25 wt %, from 1 wt % to 20 wt %, from 5 wt % to 15 wt %, or from 8 wt % to 12 wt % higher hydrocarbons, oxygen, nitrogen, carbon dioxide and/or sulfur compounds, while the remainder of the feed stream is methane. An advantage of the disclosed processes is that even very impure methane may be used as a starting material, because the non-methane based materials will ultimately be chlorinated/dehydrochlorinated to such an extent that they are readily separated from the chlorinated methanes.

In some embodiments, one or more methane purification steps may be included. Yet such methane purification steps are not contemplated to be necessary for removing ethane and/or higher hydrocarbons, since the removal of such components prior to the chlorination of methane is not required. Employment of methane purification may be desirable for methane streams that contain atypically high hydrocarbon impurities, say above 3 mole % ethane, but the extent of purification can be less stringent and less expensive than processes that do not employ the processes disclosed herein.

(b) Chlorinating Agent

The chlorinating agent may be any chlorinating known to the skilled artisan. Non-limiting examples of chlorinating agents may be chlorine gas, thionyl chloride, sulfuryl chloride, phosphorus trichloride, phosphorus pentachloride, antimony pentachloride and combinations thereof. In various embodiments, the chlorinating agent may be chlorine gas, sulfuryl chloride or combinations thereof. In another embodiment, the chlorinating agent is chlorine gas. In still another embodiment, the chlorinating agent is sulfuryl chloride.

In general, the mole ratio of methane to the chlorinating agent may range from 1:1 to about 1:20. In various embodiments, the mole ratio of methane to the chlorinating agent may range from 1:1 to about 1:20, from 1:3 to about 1:17, from 1:5 to about 1:14, or from about 1:8 to about 1:12. Lower mole ratios of methane to the chlorinating agent will produce lower chlorinated methane products such as methyl chloride and methylene chloride. Higher mole ratios of methane to the chlorinating agent will produce higher chlorinated methane products such as trichloromethane (chloroform) or carbon tetrachloride.

(c) Optional Free Radical Initiators

The chlorination of methane proceeds through a free radical mechanism. In various embodiments, free radical initiators may be used to enhance the kinetics of the process. Non-limiting examples of free radical initiators may be UV light, azo compounds such as azobisisobutyronitrile, 1,1'-azobis(cyclohexanecarbonitrile), peroxides such as di-tert-butyl peroxide, benzoyl peroxide, methyl ethyl ketone peroxide, acetone peroxide, or combinations thereof.

(d) Reaction Conditions

Generally, the process for preparing chlorinated methanes is produced by admixing in gas phase natural gas and the chlorinating agent at a temperature and pressure sufficient to produce the chlorinated methane process stream. Optionally, the process may include at least one free radical initiator to enhance the overall rate of the process.

Natural gas and the chlorinating agent are typically mixed at a space velocity ranging from 50 to 500 $min^{-1}$. In various embodiments, the space velocity of the reactants may range from 50 $min^{-1}$ to 500 $min^{-1}$, from 100 $min^{-1}$ to 300 $min^{-1}$, or from 150 $min^{-1}$ to 250 $min^{-1}$.

Natural gas and the chlorinating agent are typically mixed at a temperature and a pressure enabling the preparation of chlorinated methanes. In general, the temperature of the process may range from 200° C. to about 600° C. In various embodiments, the temperature of the process may range from 200° C. to about 600° C., from 350° C. to about 550° C., or from 400° C. to about 500° C. Generally, the pressure at which the process is conducted may range from atmospheric pressure (~14.7 psig) to about 250 psig. In various embodiments, the pressure of the process may range from 14.7 psig to about 250 psig, from about 20 psig to about 225 psig, from about 50 psig to about 200 psig, or from 75 psig to about 125 psig. In some embodiments, the chlorination of the crude methane feedstock occurs at a temperature of from 425 to 475° C., a pressure of from 50 to 200 psig, without use of a free radical initiator.

The product distribution from the chlorination of natural gas can and will vary depending on the mole ratio of the chlorinating agent to methane, the temperature of the process, the pressure of the process, and the space velocity of the process. Generally, a mixture of methyl chloride, methylene chloride, chloroform, and carbon tetrachloride are produced. Additionally, hydrogen chloride, chlorinated ethanes, chlorinated ethylenes, and higher chlorinated hydrocarbons are present in the chlorinated methane process stream.

(II) Isolation and Purification of the Chlorinated Methane Process Stream Components Still another aspect of the present disclosure encompasses purifying the chlorinated methane process stream. The process commences by first condensing the chlorinated methane process stream. The resulting process stream from the first chlorination, comprising chlorinated methanes, other chlorinated hydrocarbons, and hydrogen chloride, is fed to a condensing section wherein the temperature is reduced and at least a portion of the chlorinated components and HCl therein are condensed to a liquid phase. At least part of the condensed liquid phase may be separated and sent to a distillation train wherein the HCl and the four chlorinated methanes may be separated into individual products.

At some point in the distillation train, the process stream passes through a dehydrochlorination/chlorination reactor with a feed of a chlorinating agent. The dehydrochlorination/ chlorination reactor contains a solid catalyst, and can be a vertical packed bed or any device with sufficient hold-up, mixing, and conditions effective to provide for the dehydrochlorination (cracking) of any chlorinated ethane or higher hydrocarbons, while, or followed by, the chlorination of the dehydrochlorination products across the double bond provided by cracking.

(a) Dehydrochlorination/Chlorination Catalyst

The dehydrochlorination/chlorination catalyst may be any suitable catalyst for use in dehydrochlorination of chlorinated hydrocarbons. Non-limiting examples of suitable dehydrochlorination catalysts may be molecular sieves, alumina, activated alumina, silica, silica gel, charcoal, zeolites, diatomaceous earths, pumice, metals, metal oxides, and metal chlorides such as $FeCl_2$, $FeCl_3$, $AlCl_3$, copper, copper (I) chloride, copper (II) chloride, lead chloride, vanadium chloride, ferric oxide, and vanadium oxide. The metals, metal oxides, and metal chlorides may be loaded on solid supports. Non-limiting examples of solid supports may be aluminas, silicas, molecular sieves, activated carbon, and combinations thereof. In one embodiment, the catalyst comprises a type-Y molecular sieve, $FeCl_2$, $FeCl_3$, $AlCl_3$ or combinations thereof. In some embodiments, the catalyst is a Y-type molecular sieve. Such Y-type molecular sieves can be characterized by a relatively large pore size of about 7-10 angstroms. The $SiO_2/Al_2O_3$ molecular ratio of 2.5-6 is typical for this type of structure, which is highest of commercially available molecular sieves and imparts hydrophobic characteristics and higher acid resistance.

(b) Chlorinating Agents

Suitable chlorinating agents are described above in section (I)(b). In preferred embodiments, the chlorinating agent comprises chlorine gas and/or sulfuryl chloride.

The molar ratio of chlorinating agent to stream to be chlorinated should be high enough to ensure that substantially all mono- and dichloroethanes, chlorinated ethylenes, and higher chlorinated alkanes in the chlorinated methane process stream are consumed and converted to higher chlorinated ethanes such as tri-, tetra-, penta- or hexachlorinated ethanes. Generally, the molar ratio of the chlorinating agent to the mono- and dichloroethanes may range from 2:1 to about 20:1. In various embodiments, the molar ratio of the chlorinating agent to the mono- and dichloroethanes may range from 2:1 to about 20:1, from 4:1 to about 16:1, from about 6:1 to about 12:1, or from 8:1 to about 10:1.

(c) Reaction Conditions

The dehydrochlorination/chlorination reaction of the process stream comprising chlorinated methanes is contacted with the catalyst either in a gaseous or liquid phase. This catalyst reacts with the chlorinated alkanes preferentially and not the chlorinated methanes to dehydrochlorinate and chlorinate these species. The resulting higher chlorinated alkanes can easily be removed from the process stream by means known to the skilled artisan.

The temperature of the process is maintained at a temperature where the chlorinated process stream and the supported catalyst to provide conversion of the lower chlorinated alkanes to higher alkanes. Generally, suitable temperatures for either the gaseous phase or liquid phase may range from 100° C. to about 200° C. In various embodiments, the temperature of the dehydrochlorination/chlorination process may range from 100° C. to about 200° C., 120° C. to about 180° C., 140° C. to about 160° C., or 145° C. to about 155° C.

The pressure of the process can and will vary depending on whether the process is conducted in gaseous phase or a liquid phase. In general, the pressure of the process may range from atmospheric pressure (~14.7 psig) to about 250 psig. In various embodiments, the pressure of the process may range from 14.7 psig to about 250 psig, from 25 psig to 200 psig, from 50 psig to about 150 psig, or from 75 psig to about 125 psig.

In preferred embodiments, for gas phase dehydrochlorination/chlorination reactions, suitable temperatures may range from 100° C. to 200° C., from 125° C. to 185° C., or from 140° C. to 160° C. at pressures from atmospheric (~14.7 psig) to about 150 psig. For liquid phase dehydrochlorination/chlorination reactions temperatures of from 100° C. to 200° C., or from 120° C. to 180° C., or from 150° C. to 165° C. are employed, and pressures suitable to maintain a liquid phase may range from 100 psig to 250 psig.

Reaction time for the dehydrochlorination/chlorination process can and will vary depending on whether the process is conducted in gaseous phase or a liquid phase, the temperature of the process, the pressure of the process, and the amount of chlorinating agent used. Generally, the reaction time for the gas phase reaction may be less than 2 minutes. In various embodiments, the reaction time for the gas phase reaction may be less than 2 minutes, less than 1 minute, less than 30 seconds, or less than 10 seconds. In general, the reaction time for the liquid phase reaction may be less than 2 hours. In various embodiments, the reaction time for the liquid phase reaction may be less than 2 hours, less than 1 hour, or less than 30 minutes.

While the chlorinated methane are essentially unaffected by the reaction conditions of the dehydrochlorination/chlorination reaction, close to 100% conversion of any chlorinated ethane byproducts is expected. More particularly, at such conditions, any mono- or dichlorinated ethanes or chlorinated ethylenes present in the process stream after the initial chlorination step are expected to dehydrochlorinate to provide stoichiometric amounts of ethylene or vinyl chloride. The generated ethylene and vinyl chloride are chlorinated to provide predominantly di- and trichloroethane, which can undergo further sequential cracking/chlorination to form tetra-, penta- and hexachlorinated ethanes. The cracking and chlorination reactions occur simultaneously, meaning that olefinic species can be chlorinated while non-olefinic species are cracking. Although the cracking and chlorination reactions of a given feed molecule are sequential, it is not required to complete the cracking reaction of a given feed component before the chlorination of its cracking products ensues.

The process may also include suitable condensing, vaporizing or separation steps.

Figure 1:
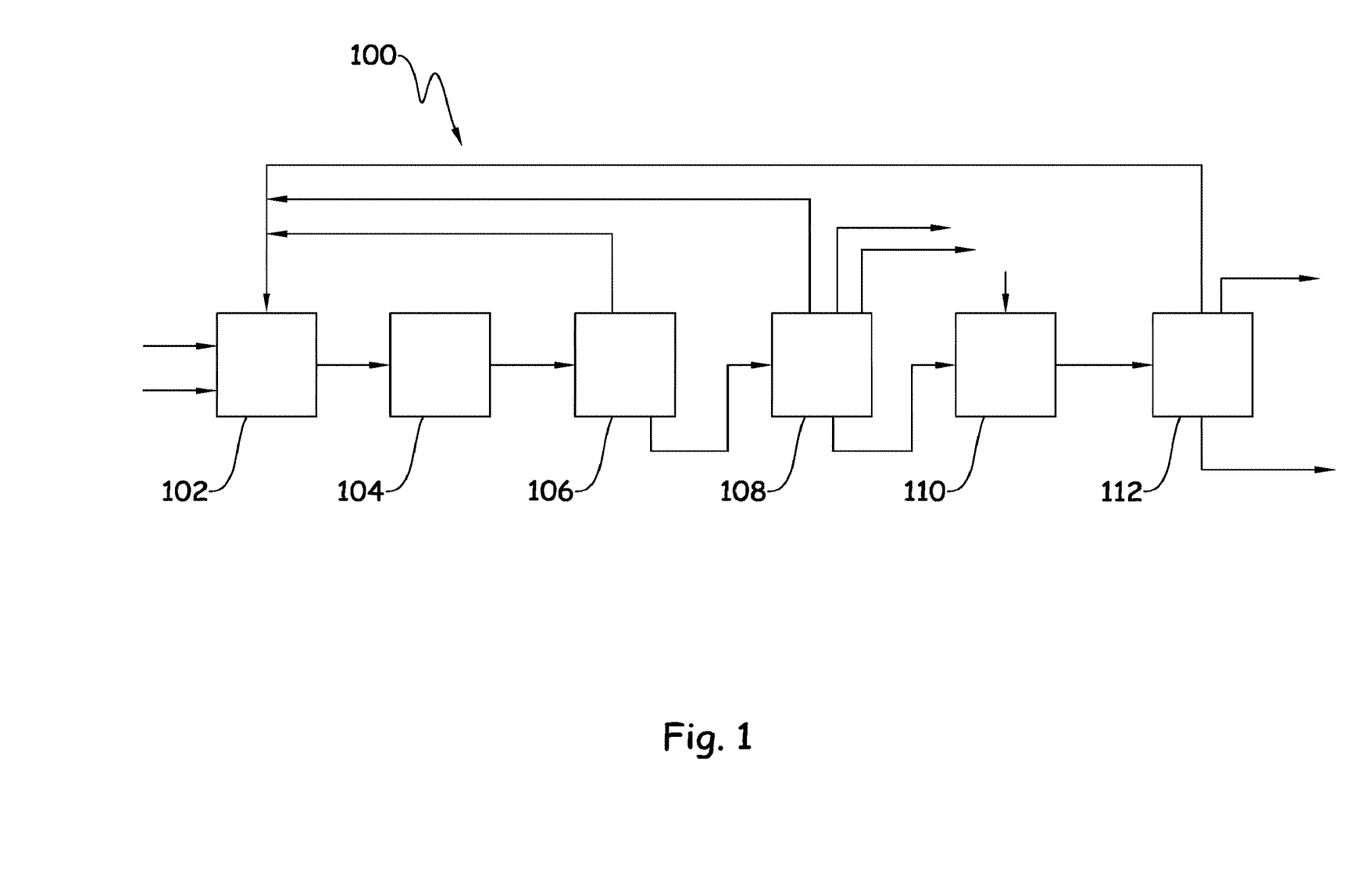
FIG. 1 shows a schematic representation of a process according to one embodiment of the invention.

A schematic illustration of such a process is shown in FIG. 1. As shown in FIG. 1, in process 100 methane or natural gas and chlorine are fed to a thermal chlorination reactor 102 operating at from 425° C. to 475° C. and 75 to 175 psig. The process stream from chlorination reactor 102 comprises chlorinated methanes, chlorinated ethanes, chlorinated ethylenes, chlorinated higher hydrocarbons, HCl and any unreacted methane. Typically, such reactors are operated at essentially complete chlorine conversion, but small amounts of unreacted chlorine may also be present. The process stream from chlorination reactor 102 then passes through a cooling train 104, including, e.g., heat recovery devices such as hot oil heaters, air, and/or water cooled heat exchangers, and refrigerated heat exchangers.

The cooled process stream then enters a gas/liquid separator 106 from which at least a portion of any unreacted methane and HCl, and optionally a portion of chlorinated methanes are recovered as a gaseous stream and recycled to the thermal chlorination reactor 102. This stream can, optionally, be cross exchanged (not shown) with the process stream from the reactor in the cooling train to recover refrigeration value. The condensed liquid from gas/liquid separator 106, comprising at least part of the chlorinated methane products, at least part of the chlorinated ethanes, ethylenes and chlorinated higher hydrocarbons and at least a portion of the HCl, is fed to a distillation train 108 which can include any number of distillation columns.

In the embodiment shown, distillation train 108 is equipped and configured to provide overhead streams comprising HCl, methyl chloride and dichloromethane, or blends of these components, any of which streams may be recycled in whole or in part to thermal chlorination reactor 102 or may be subjected to further distillation or other processing. The bottoms, liquid product stream provided by distillation train 108, typically containing chloroform and carbon tetrachloride, as well as chlorinated ethanes, ethylenes and chlorination products of higher hydrocarbons, is provided to catalytic cracking/chlorination reactor 110, which is also fed with chlorine.

Within catalytic cracking/chlorination reactor 110, chlorinated ethane and chlorinated higher alkanes are dehydrochlorinated (cracked) and chlorinated to provide heavier components, such as 1,1,2-trichloroethane or 1,1,2,2-tetrachloroethane. The product from cracking/chlorination reactor 110 is fed to distillation train 112, which may include any number of distillation columns.

Distillation train 112 includes at least one distillation column operated at conditions effective to provide a bottoms stream comprising carbon tetrachloride and chlorinated ethanes and ethylenes as well as higher compounds, such as chlorinated propanes and butanes produced in the process. The overhead product streams from distillation train 112 will typically contain chloroform, HCl and any unreacted chlorine, any of which may be recycled in part or in whole to reactor 102 or subjected to further distillation or other processing steps (not shown).

In some alternative embodiments (not shown), the bottoms stream from distillation train 108 can be vaporized and provided to cracking/chlorination reactor 110 and cracking/chlorination can be carried out in the gas phase. In still other alternative embodiments (not shown), reactor 110 can be relocated within distillation train 108 to treat streams that also contain methyl chloride and/or dichloromethane.

Definitions

When introducing elements of the embodiments described herein, the articles "a", "an", "the" and "said" are intended to mean that there are one or more of the elements. The terms "comprising", "including" and "having" are intended to be inclusive and mean that there may be additional elements other than the listed elements.

The term "alkane" as used herein describes saturated hydrocarbyl groups that contain from 1 to 30 carbon atoms. They may be linear, branched, or cyclic, may be substituted as defined below, and include methyl, ethyl, propyl, isopropyl, butyl, hexyl, heptyl, octyl, nonyl, and the like.

If ranges are disclosed, the endpoints of all ranges directed to the same component or property are inclusive and independently combinable (e.g., ranges of "up to 25 wt. %, or, more specifically, 5 wt. % to 20 wt. %," is inclusive of the endpoints and all intermediate values of the ranges of "5 wt. % to 25 wt. %," etc.).

The terms "dehydrochlorination" and "cracking" may be used interchangeably and refer to a process of removing a hydrogen and chlorine, or hydrogen chloride, from a compound.

The phrase "chlorinated ethylenes" refers to ethylene having one or more chlorine atoms attached.

The phrase "higher chlorinated ethanes" refers to ethanes having more than two chlorine atoms attached. Higher chlorinated ethanes include trichlorinated, tetrachlorinated, pentachlorinated and hexachlorinated ethanes.

The phrase "higher alkanes" refer to compounds having more than 2 carbons. Higher alkanes may be linear or branched and may include but not limited to propane, isobutane, butane, pentane, isopentane, neopentane, hexane, heptane, and alike.

The phrase "higher chlorinated alkanes" refers to the "higher alkanes" described above having one or chlorine atoms attached.

The abbreviation "vinyl" refers to vinyl chloride.
The abbreviation "A-Di" refers to 1,1-dichloroethane.
The abbreviation "B-tri" refers to 1,1,2-trichloroethane.
The abbreviation "Unsym" refers to 1,1,1,2-tetrachloroethane.
The abbreviation "Sym" refers to 1,1,2,2-tetrachloroethane.

Having described the invention in detail, it will be apparent that modifications and variations are possible without departing from the scope of the invention defined in the appended claims.

EXAMPLES

The following examples illustrate various embodiments of the invention.

Example 1: Preparation of Chlorinated Methanes from a Natural Gas Feed Stream

Into a chlorination reactor, natural gas and chlorine may be introduced. The mole ratio of chlorine gas to methane may be approximately 20:1. The pressure of the reactor may be 100 psig and a temperature may be maintained at 450° C. The process stream exiting the chlorination reactor may be cooled, and then may be analyzed by GC/MS. The analysis of the sample may show a mixture of methyl chloride, methylene chloride, chloroform, carbon tetrachloride, chloroethane, vinyl chloride, 1,1,-dichloroethane, 1,2-dichloroethane, trichloroethylene, tetrachloroethylene, hexachloroethane, hydrogen chloride, and unreacted methane.

Example 2: Simultaneous Gas-phase Dehydrochlorination and Chlorination of the Chlorinated Methane Process Stream The chlorinated methane process stream (from example 1) may be introduced into a cooling train (104, FIG. 1) and enters the gas/liquid separator 106. Unreacted methane and hydrogen chloride may be separated from the liquid components which may comprise chlorinated methanes, chlorinated ethylenes, chlorinated ethanes, and a portion of hydrogen chloride. This liquid sample may be fed into distillation train 108. Lower boiling point materials such as methyl chloride, methylene chloride, and hydrogen chloride may be removed. The higher boiling point materials may then be introduced into catalytic dehydrochlorination/chlorination reactor 110 packed with Y-type zeolite 1/16" extrudates which is fed with a stream of chlorine gas. The catalytic dehydrochlorination/chlorination reactor 110 may be maintained at a temperature of 150° C. and atmospheric pressure. The reactor effluent may be cooled to 0° C. and a sample may be analyzed by GC/MS. The GC/MS may show the relative amounts of chloroform and carbon tetrachloride may not have changed while the quantities of chloroethane, and dichloroethane may now be present in ppm quantities, and quantities of trichloroethane, tetrachloroethane, pentachloroethane, and hexachloroethane may be present.

Figure 2:
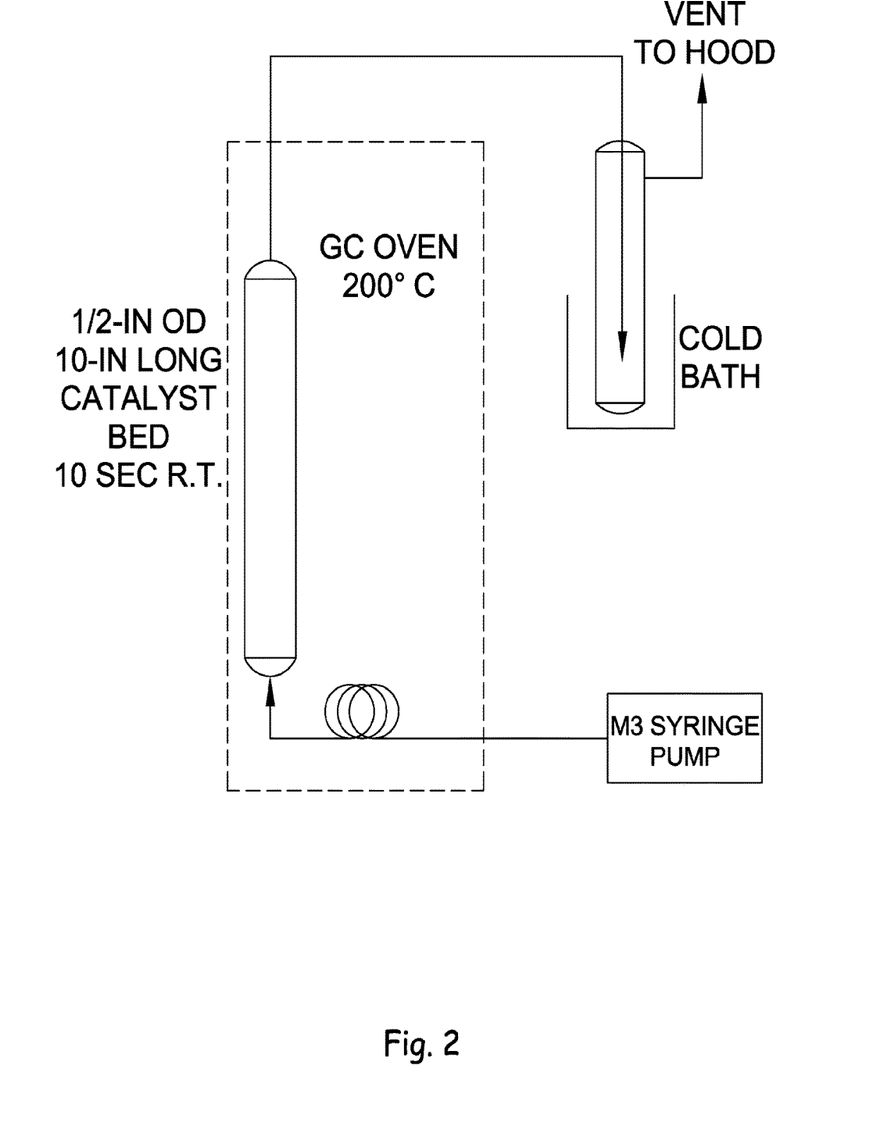
FIG. 2 is a graphical representation of a lab-scale gas-phase catalytic reactor configuration.

Example 3: Simultaneous Gas-phase Dehydrochlorination and Chlorination of 1,1-Dichloroethane A solution of 1 wt % 1,1-dichloroethane in chloroform was prepared, and the solution divided into two portions. 4 wt % Sulfuryl chloride was added to a first portion and both portions were pumped independently at 10-30 liquid cc/hour into a vaporizer and reactor as shown in FIG. 2. The reactor was 1.09 cm ID and 25.4 cm long, packed with Y-type zeolite 1/16" extrudates. Reactor temperature was 125° C.-200° C. and pressure was atmospheric pressure. The reactor effluent was cooled and condensed at 0° C. and samples of the condensed effluent were analyzed by GC/MS.

Figure 3:
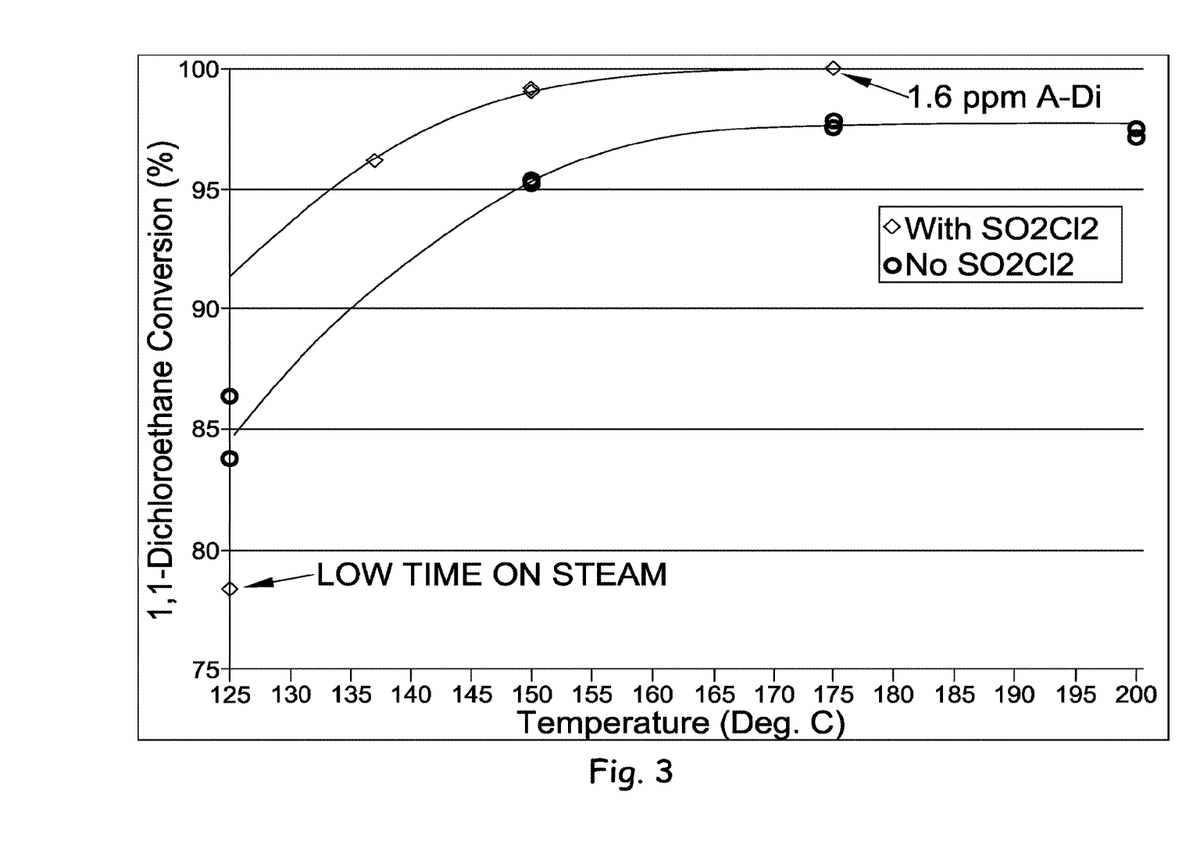
FIG. 3 is a graphical depiction of the effect of increasing temperature on the conversion of 1,1,-dichloroethane at a 10 second residence time as seen in some embodiments of the process.
Figure 4:
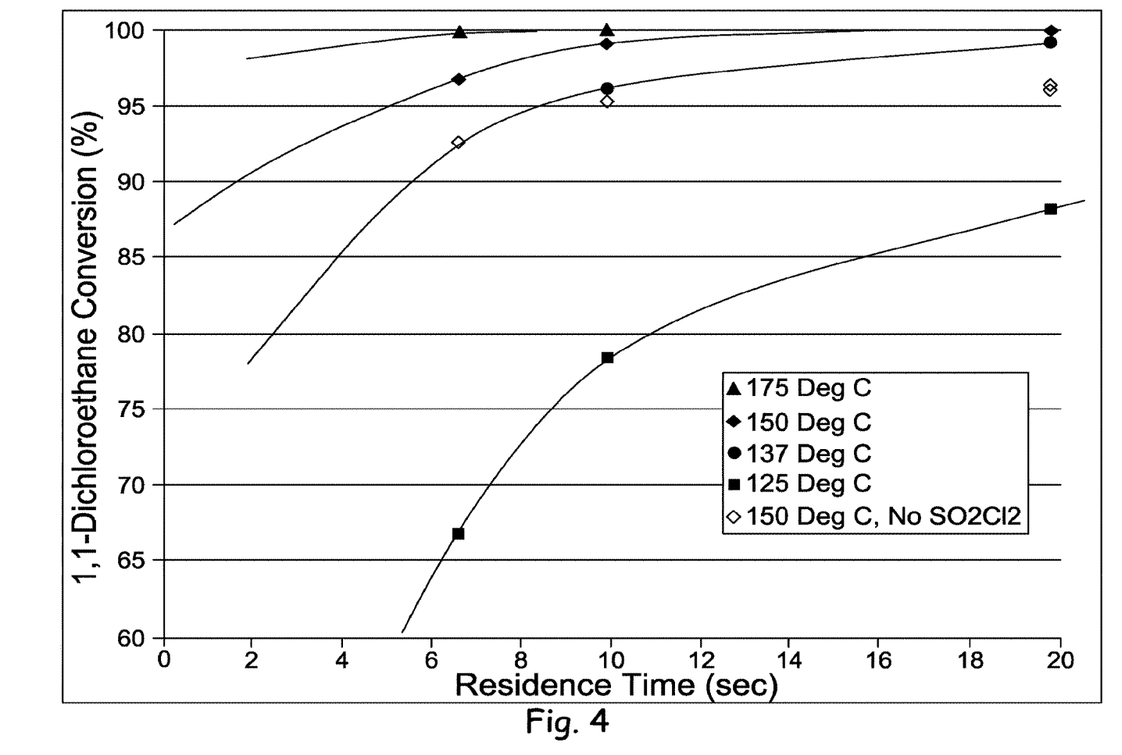
FIG. 4 is a graphical depiction of the effect of increasing residence time on the conversion of 1,1,-dichloroethane at different temperatures as seen in some embodiments of the process.

As shown in FIG. 3, at a residence time of about 10 s and temperature of 175° C., most of the 1,1,-dichloroethane without sulfuryl chloride reacted as shown in Table 1 below. With sulfuryl chloride present, 1,1,-dichloroethane completely reacted at these conditions as shown in Table 2 below. In FIGS. 3 and 4, the cases without sulfuryl chloride were for comparison only, and demonstrate that the dehydrochlorination reaction alone becomes equilibrium limited. This data also shows that chlorination needs to occur substantially simultaneously in order to overcome the cracking equilibrium and to provide essentially complete conversions.

TABLE 1

Gas Phase Results without Sulfuryl Chloride

| Sample Name | Time | Temp (Deg C.) | Feed (cc/Hr) |
|---|---|---|---|
| Feed 1% A-Di | | | |
| 125b | 16:17 | 125 | 20 |
| 125b reshot | 16:17 | 125 | 20 |
| 150d | 16:36 | 150 | 20 |
| 150d reshot | 16:36 | 150 | 20 |
| 175 | 16:01 | 175 | 20 |
| 175 reshot | 16:01 | 175 | 20 |
| 200 | 15:45 | 200 | 20 |
| 200 reshot | 15:45 | 200 | 20 |

| Sample Name | TIC area Vinyl | TIC area t-1,2-Dichloro-ethylene | TIC area 11-Dichloro-Ethane (A-Di) | TIC area Trichloro-ethylene | TIC area 112-Trichloro-ethane | TIC area 1122-Tetra-chloro-ethane | TIC area Hexa-chloro-ethane | A-Di Conv (%) |
|---|---|---|---|---|---|---|---|---|
| Feed 1% A-Di | 0.03 | 0.12 | 125.91 | 0.01 | 0.48 | 0.20 | 9.04 | |
| 125b | 38.24 | 0.53 | 17.16 | 0.59 | 3.93 | 0.12 | 0.28 | 86.37 |
| 125b reshot | 42.78 | 0.65 | 20.41 | 0.70 | 4.76 | 0.15 | 0.34 | 83.79 |
| 150d | 45.32 | 2.12 | 5.82 | 1.21 | 11.04 | 0.29 | 0.83 | 95.37 |
| 150d reshot | 43.94 | 2.16 | 5.99 | 1.27 | 11.77 | 0.28 | 0.89 | 95.25 |
| 175 | 39.24 | 1.51 | 3.09 | 0.35 | 6.38 | 0.26 | 1.67 | 97.54 |
| 175 reshot | 33.29 | 1.33 | 2.78 | 0.31 | 5.82 | 0.24 | 1.47 | 97.79 |
| 200 | 35.29 | 2.65 | 3.22 | 0.31 | 13.99 | 0.93 | 1.99 | 97.44 |
| 200 reshot | 37.11 | 2.95 | 3.63 | 0.16 | 16.82 | 1.14 | 2.47 | 97.12 |

TABLE 2

Gas Phase Results with Sulfuryl Chloride

| Sample Name | Time | Temp (Deg C.) | Feed (cc/Hr) |
|---|---|---|---|
| Feed: 1% A-Di + SO$_2$Cl$_2$ | | | |
| 125 | 11:07 | 125 | 20 |
| 137 | 12:52 | 137 | 20 |
| 150c | 12:42 | 150 | 20 |
| 150c reshot | 12:42 | 150 | 20 |
| 175 | 10:52 | 175 | 20 |

| Sample Name | TIC area Vinyl | TIC area 11-Dichloro-Ethane (A-Di) | TIC area Trichloro-ethylene | TIC area 112-Trichloro-ethane | TIC area 1112-Tetra-chloro-ethane | TIC area 1122-Tetra-chloro-ethane | TIC area Penta-chloro-ethane | TIC area Hexa-chloro-ethane | A-Di Conv (%) |
|---|---|---|---|---|---|---|---|---|---|
| Feed: 1% A-Di + SO$_2$Cl$_2$ | 0.08 | 145.87 | 0.0330 | 0.62 | 0.00 | 0.33 | 0.04 | 6.67 | |

TABLE 2-continued

| | | | Gas Phase Results with Sulfuryl Chloride | | | | | |
|---|---|---|---|---|---|---|---|---|
| 125 | 0.000 | 31.53 | 0.0071 | 123.42 | 9.48 | 75.07 | 7.21 | 1.77 | 78.38 |
| 137 | 0.008 | 5.60 | 0.0000 | 56.97 | 4.62 | 71.59 | 7.64 | 2.40 | 96.16 |
| 150c | 0.000 | 1.42 | 0.0123 | 126.44 | 0.97 | 71.30 | 6.94 | 2.09 | 99.02 |
| 150c reshot | 0.022 | 1.23 | 0.0000 | 118.58 | 5.26 | 71.17 | 8.50 | 2.81 | 99.16 |
| 175 | 2.266 | 0.02 | 0.0000 | 71.39 | 6.52 | 88.36 | 9.08 | 4.53 | 99.98 |

Figure 5:
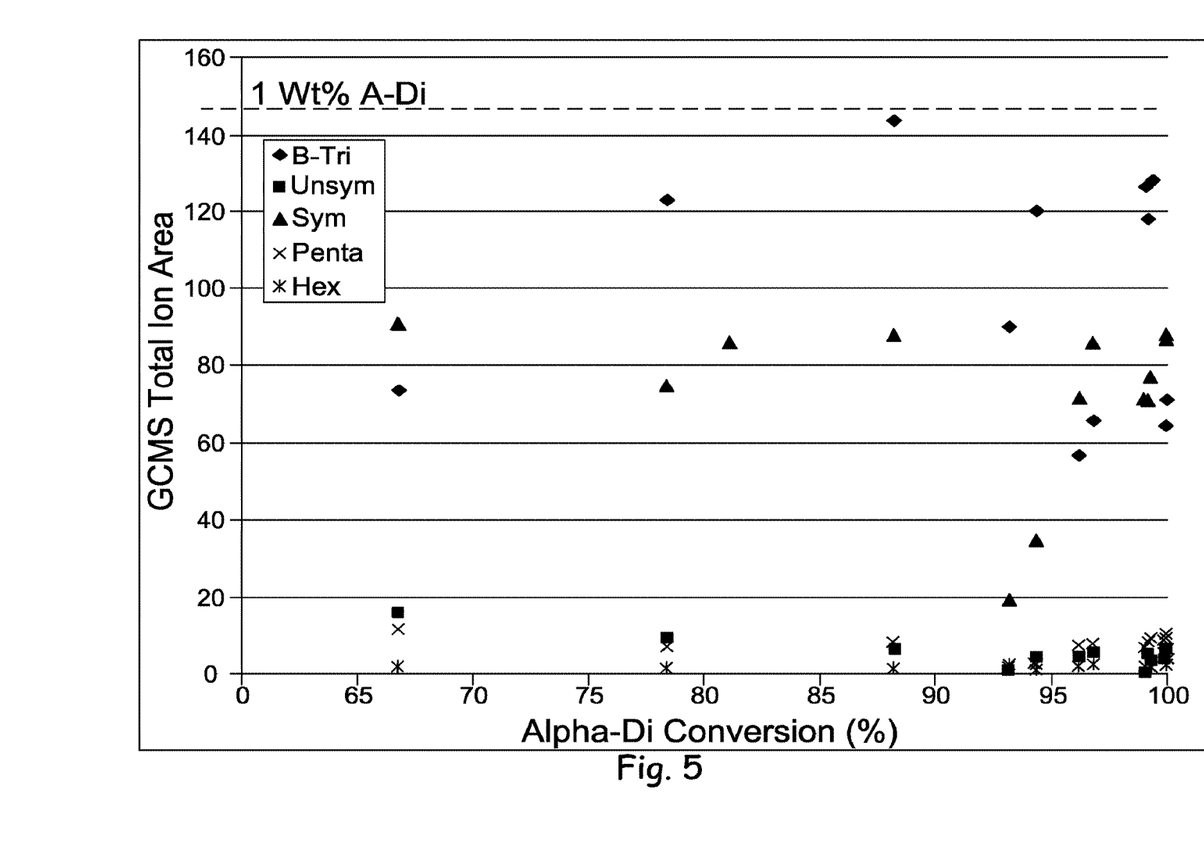
FIG. 5 is a graphical depiction of the products produced as a function of the conversion of 1,1,-dichloroethane as seen in some embodiments of the process.

Tables 3 with varying residence time and Table 4 with varying residence time and temperature show the data with and without sulfuryl chloride. FIG. 4 shows that complete conversion of 1,1-dichloroethane occurred at 150° C. if the residence time was increased to 20 seconds, while FIG. 5 shows the distribution of higher chlorinated ethanes that were produced with sulfuryl chloride. In the legend of FIG. 5, the abbreviation B-tri indicates 1,1,2-trichloroethane, Unsym indicates 1,1,1,2-tetrachloroethane and Sym indicates 1,1,2,2-tetrachloroethane.

TABLE 3

| | | | Gas Phase Results without Sulfuryl Chloride. | | |
|---|---|---|---|---|---|
| Sample Name | | Time | Temp (Deg C.) | Feed (cc/Hr) | Res. Time (s) |
| Feed 1% A-Di | | | | | |
| 150/10a | | 16:55 | 150 | 10 | 19.80 |
| 150/10b | | 16:57 | 150 | 10 | 19.80 |
| 150d | | 16:36 | 150 | 20 | 9.90 |
| 150d reshot | | 16:36 | 150 | 20 | 9.90 |
| 150/30 | | 17:03 | 150 | 30 | 6.60 |

| Sample Name | TIC area Vinyl | TIC area t-1,2-Dichloro-ethylene | TIC area 11-Dichloro-Ethane (A-Di) | TIC area Trichloro-ethylene | TIC area 112-Trichloro-ethane | TIC area 1122-Tetra-chloro-ethane | TIC area Hexa-chloro-ethane | Res. Time (s) | A-Di Conv (%) |
|---|---|---|---|---|---|---|---|---|---|
| Feed 1% A-Di | 0.03 | 0.12 | 125.91 | 0.01 | 0.48 | 0.20 | 9.04 | | |
| 150/10a | 40.42 | 1.71 | 4.65 | 1.17 | 7.74 | 0.30 | 0.84 | 19.80 | 96.31 |
| 150/10b | 39.99 | 1.81 | 4.94 | 1.22 | 7.94 | 0.32 | 0.94 | 19.80 | 96.07 |
| 150d | 45.32 | 2.12 | 5.82 | 1.21 | 11.04 | 0.29 | 0.83 | 9.90 | 95.37 |
| 150d reshot | 43.94 | 2.16 | 5.99 | 1.27 | 11.77 | 0.28 | 0.89 | 9.90 | 95.25 |
| 150/30 | 48.31 | 1.94 | 9.39 | 1.13 | 8.02 | 0.32 | 0.90 | 6.60 | 92.54 |

TABLE 4

| | Gas Phase Results using Sulfuryl Chloride | | | |
|---|---|---|---|---|
| Sample Name | | Time | Temp (Deg C.) | Feed (cc/Hr) |
| Feed: 1% A-Di + SO$_2$Cl$_2$ | | | | |
| 125/30 | | 12:21 | 125 | 30 |
| 125 | | 11:07 | 125 | 20 |
| 125/10 | | 11:33 | 125 | 10 |
| 137 | | 12:52 | 137 | 20 |
| 137/10 | | 13:14 | 137 | 10 |
| 150/30 | | 12:09 | 150 | 30 |
| 150c | | 12:42 | 150 | 20 |
| 150c reshot | | 12:42 | 150 | 20 |
| 150/10 | | 11:55 | 150 | 10 |
| 173/30 | | 13:22 | 173 | 30 |
| 175 | | 10:52 | 175 | 20 |

| Sample Name | TIC area Vinyl | TIC area 11-dichloro-Ethane (A-Di) | TIC area 112-Trichloro-ethylene | TIC area 112-Trichloro-ethane | TIC area 1112-Tetra-chloro-ethane | TIC area 1122-Tetra-chloro-ethane | TIC area Penta-chloro-ethane | TIC area Hexa-chloro-ethane | Res. Time (s) | A-Di Conv (%) |
|---|---|---|---|---|---|---|---|---|---|---|
| Feed: 1% A-Di + SO$_2$Cl$_2$ | 0.08 | 145.87 | 0.0330 | 0.62 | 0.00 | 0.33 | 0.04 | 6.67 | | |

TABLE 4-continued

| Gas Phase Results using Sulfuryl Chloride | | | | | | | | | |
|---|---|---|---|---|---|---|---|---|---|
| 125/30 | 0.000 | 48.49 | 0.0000 | 74.30 | 16.11 | 91.30 | 11.52 | 2.24 | 6.60 66.76 |
| 125 | 0.000 | 31.53 | 0.0071 | 123.42 | 9.48 | 75.07 | 7.21 | 1.77 | 9.90 78.38 |
| 125/10 | 0.000 | 17.23 | 0.0168 | 143.31 | 6.71 | 88.06 | 8.16 | 1.70 | 19.80 88.19 |
| 137 | 0.008 | 5.60 | 0.0000 | 56.97 | 4.62 | 71.59 | 7.64 | 2.40 | 9.90 96.16 |
| 137/10 | 0.000 | 1.08 | 0.0072 | 127.49 | 3.71 | 77.29 | 9.18 | 2.37 | 19.80 99.26 |
| 150/30 | 0.000 | 4.70 | 0.0097 | 66.04 | 5.86 | 86.24 | 7.63 | 2.58 | 6.60 96.78 |
| 150c | 0.000 | 1.42 | 0.0123 | 126.44 | 0.97 | 71.30 | 6.94 | 2.09 | 9.90 99.02 |
| 150c reshot | 0.022 | 1.23 | 0.0000 | 118.58 | 5.26 | 71.17 | 8.50 | 2.81 | 9.90 99.16 |
| 150/10 | 2.372 | 0.12 | 0.0000 | 64.63 | 7.06 | 87.10 | 10.29 | 2.72 | 19.80 99.92 |
| 173/30 | 2.689 | 0.18 | 0.0084 | 71.29 | 4.10 | 88.35 | 9.11 | 5.18 | 6.60 99.87 |
| 175 | 2.266 | 0.02 | 0.0000 | 71.39 | 6.52 | 88.36 | 9.08 | 4.53 | 9.90 99.98 |

Figure 6:
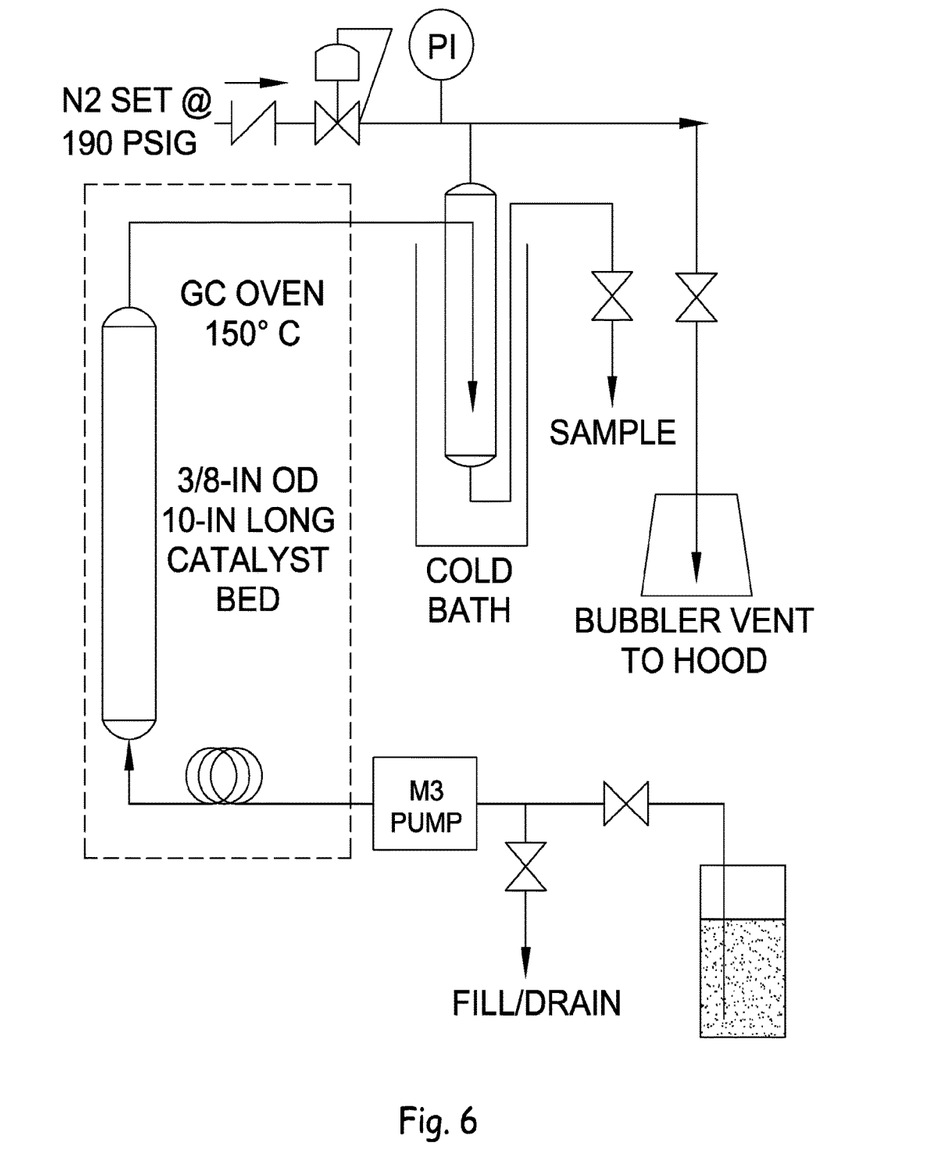
FIG. 6 is a graphical representation of a lab-scale liquid-phase catalytic reactor configuration.

Example 4: Simultaneous Liquid-phase Dehydrochlorination and Chlorination of 1,1-Dichloroethane A solution of 1 wt % 1,1-dichloroethane in chloroform was prepared. 4 wt % Sulfuryl chloride was added and the solution was pumped at 12-30 liquid cc/hour into a reactor as shown in FIG. 6. The reactor was 0.77 cm ID and 25.4 cm long, packed with Y-type zeolite 1/16" extrudates. For more efficient packing into the narrow bore reactor, the length of the extrudates was reduced with grinding and the portion that was retained above a 0.0331-inch screen was used. Reactor temperature was 150-165° C. and pressure was 195 psig. The reactor effluent was cooled to 0° C. and samples of the cooled effluent were analyzed by GC/MS. The results of this analysis are shown in Table 5, below. As can be seen by the last entry, conversion of 1,1-dichloroethane in excess of 99% were seen, with a remaining concentration of 1,1-dichloroethane of less than 100 ppm by weight.

TABLE 5

| Liquid phase reaction results | | | | |
|---|---|---|---|---|
| Time (Military) | Flow (cc/m) | Temp (° C.) | 1,1-dichloroethane conversion (%) | 1,1-dichloroethane remaining (ppm) |
| 1105 | 0.33 | 150 | 74.10 | 2720 |
| 1135 | 0.33 | 150 | 88.95 | 1160 |
| 1203 | 0.33 | 150 | 91.26 | 918 |
| 1232 | 0.33 | 165 | 98.36 | 172 |
| 1300 | 0.33 | 165 | 95.35 | 488 |
| 1336 | 0.33 | 165 | 99.44 | 58 |

Example 5: Simultaneous Gas-phase Dehydrochlorination and Chlorination of 1,1-Dichloroethane A solution was prepared containing 97.5 g chloroform, 1.01 g 1,1-dichloroethane, 0.50 g 1,2-dichloropropane, 0.253 g 2-chloropropane, 0.246 g 1-chloropropane, 0.492 g bromochloromethane, and 9.50 g sulfuryl chloride. The solution was pumped at 11.8 liquid cc/hour into a vaporizer and reactor as shown in FIG. 2. The reactor was 1.09 cm ID and 25.4 cm long, packed with Y-type zeolite 1/16" extrudates. Reactor temperature was 150° C.-190° C. and pressure was atmospheric. The reactor effluent was cooled and condensed at 0° C. and samples of the condensed effluent were analyzed by GCMS. As shown in Table 6, all of the chlorinated ethane and propane components were essentially completely destroyed at 190° C., except for bromochloromethane, for which the data were inconclusive.

TABLE 6

| Gas Phase Reaction Rssults | | | | |
|---|---|---|---|---|
| Temp (Deg C.) | 2-Chloropropane Conversion (%) | 1-Chloropropane Conversion (%) | A-Di Conversion (%) | 1,2-Dichloropropane Conversion (%) |
| 150 | 100 | 100 | 90.37 | 94.24 |
| 150 | 99.91 | 100 | 85.87 | 72.55 |
| 150 | 100 | 100 | 88.73 | 85.48 |
| 150 | 100 | 100 | 90.31 | 80.10 |
| 150 | 100 | 100 | 92.31 | 93.97 |
| 170 | 100 | 100 | 98.56 | 98.32 |
| 190 | 100 | 100 | 99.96 | 99.69 |

Example 6: Simultaneous Gas-phase Dehydrochlorination and Chlorination of 1,1-Dichloroethane A solution of 1 wt % 1,1-dichloroethane in chloroform may be prepared and introduced into a pressure reactor. Chlorine gas may be introduced into the reactor as shown in FIG. 6. The reactor may be 1.09 cm ID and 25.4 cm long, packed with Y-type zeolite 1/16" extrudates. Reactor temperature may range from 125° C.-200° C. and pressure may be atmospheric pressure. After 1 hour, the reactor effluent may be cooled and condensed at 0° C. and samples of the condensed effluent may be analyzed by GC/MS. The GC/MS may show the conversion of 1,1-dichloroethane in excess of 99% may be seen, with a remaining concentration of 1,1-dichloroethane may be less than 60 ppm by weight.

Example 7: Simultaneous Gas-phase Dehydrochlorination and Chlorination of 1,2-Dichloroethane A solution of 1 wt % 1,2-dichloroethane in carbon tetrachloride may be prepared, and the solution may be divided into two portions. 4 wt % Sulfuryl chloride may be added to a first portion and both portions may be pumped at 10-30 liquid cc/hour into a vaporizer and reactor as shown in FIG. 6. The reactor may be 1.09 cm ID and 25.4 cm long, packed with Y-type zeolite 1/16" extrudates. Reactor temperature may range from 125° C.-200° C. and pressure may be atmospheric pressure. The reactor effluent may be cooled and condensed at 0° C. and samples of the condensed effluent may be analyzed by GC/MS. The GC/MS may show the conversion of 1,2-dichloroethane in excess of 99% may be seen, with a remaining concentration of 1,2-dichloroethane may be less than 100 ppm by weight.

What is claimed is:

1. A process for the production of chlorinated methanes comprising chlorinating a feedstream comprising methane and ethane to produce a process stream comprising chlorinated methanes and mono- and dichlorinated ethanes; and subjecting at least a portion of the process stream to conditions effective to dehydrochlorinate and chlorinate at least a portion of the mono- and dichlorinated ethanes in the process stream to higher chlorinated ethanes.

2. The process of claim 1, wherein the dichlorinated ethane comprises 1,1-dichloroethane.

3. The process of claim 1, wherein greater than 95% of the dichlorinated ethane is converted to higher chlorinated ethanes.

4. The process of claim 1, wherein greater than 98% of the dichloroethane is converted to higher chlorinated ethanes.

5. The process of claim 1, wherein the mono- and dichlorinated ethanes are simultaneously dehydrochlorinated and chlorinated in the same reactor.

6. The process of claim 1, wherein the dehydrochlorination is carried out in the presence of a catalyst.

7. The process of claim 6, wherein the catalyst is selected from the group consisting of molecular sieves, aluminas, silicas, and metals, metal oxides or metal halides loaded on supports including aluminas, silicas and activated carbon.

8. The process of claim 6 wherein the catalyst comprises a type-Y molecular sieve, $FeCl_2$, $FeCl_3$, $AlCl_3$ or combinations thereof.

9. The process of claim 1, wherein the chlorination is carried out in the presence of a chlorinating agent.

10. The process of claim 9, wherein the chlorinating agent comprises at least one of sulfuryl chloride or chlorine.

11. The process of claim 9, wherein the chlorinating agent comprises chlorine and an excess of chlorine is used.

12. The process of claim 1, further comprising separating at least one higher chlorinated ethane from the process stream to provide a product stream comprising methyl chloride, dichloromethane, trichloromethane and/or tetrachloromethane.

13. The process of claim 1, wherein the product stream consists essentially of chlorinated methanes.

14. The process of claim 1, wherein the product stream contains less chlorinated ethanes than the process stream from the methane chlorination reactor.

15. The process of claim 1, wherein the dehydrochlorination and chlorination is carried out in the gas phase.

16. The process of claim 1, wherein the dehydrochlorination and chlorination is carried out in the liquid phase.

17. The process of claim 1, wherein the mono- and dichlorinated ethanes are dehydrochlorinated and chlorinated in the same reactor, and the dehydrochlorination is carried out in the presence of a catalyst.

18. The process of claim 1, wherein the chlorinating agent comprises chlorine, and further comprises separating at least one higher chlorinated ethane from the process stream to provide a product stream comprising methyl chloride, dichloromethane, trichloromethane and/or tetrachloromethane.

19. The process of claim 1, wherein the dichlorinated ethane comprises 1,1-dichloroethane, greater than 95% of the dichlorinated ethane is converted to higher chlorinated ethanes, and the mono- and dichlorinated ethanes are dehydrochlorinated and chlorinated in the same reactor.

* * * * *